United States Patent [19]

Lapota et al.

[11] Patent Number: 4,978,854
[45] Date of Patent: Dec. 18, 1990

[54] BIOLUMINESCENT DETECTOR

[75] Inventors: David Lapota; Gary F. Mastny, both of San Diego; Hugh D. Copeland, Chula Vista, all of Calif.

[73] Assignee: The United States of America as represented by the Secretary of the Navy, Washington, D.C.

[21] Appl. No.: 395,239

[22] Filed: Aug. 16, 1989

[51] Int. Cl.⁵ ............................................. G01N 21/76
[52] U.S. Cl. ................................... 250/361 C; 422/52
[58] Field of Search ...................... 422/52; 250/361 C

[56] References Cited

U.S. PATENT DOCUMENTS

| | | |
|---|---|---|
| 3,359,973 | 12/1967 | Hoffman . |
| 3,746,513 | 7/1973 | Warnick et al. . |
| 3,797,999 | 3/1974 | Witz et al. ...................... 250/361 C |
| 4,329,316 | 5/1982 | Wladimiroff et al. ................. 422/52 |
| 4,350,890 | 9/1982 | Geelhood et al. .............. 250/361 C |
| 4,563,331 | 1/1986 | Losee et al. ........................... 422/52 |

FOREIGN PATENT DOCUMENTS 2167181   5/1986   United Kingdom ............ 250/361 C

OTHER PUBLICATIONS

Lapota et al, "Observations of Bioluminescence in Marine Plankton from the Sea of Cortez", J. Exp. Mar. Ecol., 77, 1984, pp. 209-240.

Aiken et al., "A Solid State Sensor for Mapping and Profiling Stimulated Bioluminescence in the Marine Environment", Continental Shelf Research, 1 (1), pp. 1-14, 1984, Pergamon Press.

Final Rpt., Expendable Optical Profiler, Sippican Ocean Systems, Marion, MA, undated.

Brochure, "Sippican Expendable Profiling Systems", Sippican Ocean Systems, Marion, MA, undated.

Primary Examiner—Carolyn E. Fields
Attorney, Agent, or Firm—Harvey Fendelman; Thomas Glenn Keough; Michael A. Kagan

[57] ABSTRACT

A bioluminescent detector is disclosed for detecting and measuring in situ bioluminescence generated by marine microorganisms. The detector includes a laminar flow chamber, a turbulent flow chamber in fluid communication with the laminar flow chamber, and a photon detector network positioned with the turbulent flow chamber. The detector is dropped over the side of a ship which may be underway and sinks at constant velocity. As the detector descends, ocean water flows through the laminar flow chamber and then into the turbulent flow chamber where fluid turbulence subjects any bioluminescent organisms present to shear stress, causing them to generate photons that are detected by the photon detector network.

26 Claims, 3 Drawing Sheets

BIOLUMINESCENT DETECTOR

STATEMENT OF GOVERNMENT INTEREST

The invention described herein may be manufactured and used by or for the Government of the United States of America for governmental purposes without the payment of any royalties thereon or therefor.

BACKGROUND OF THE INVENTION

The present invention generally relates to the field of detecting and measuring marine bioluminescence. Specifically the present invention relates to in situ measurement of marine bioluminescence intensity in the upper surface waters of the oceans.

Marine bioluminescence has been measured both at the surface of the ocean and at depths by various photomultiplier tubes in bathyphotometer assemblies. [See Bityukov, E.P., Rybasov, V.P., and Shayda, V.G., "Annual Changes In The Bioluminescence Field Intensity In The Neritic Zone Of The Black Sea," *Oceanology,* Vol. 7(6), pp. 848–856, 1967; Gitel'zon I.I., Baklanov, O.G., Filimov, V.S., Artemkin, A.S., and Shatokhin, V.F., "Bioluminscence As A Hydrooptical And Biological Factor In The Sea," *Works Of The Moscow Society of Naturalists, Bioluminescence,* Vol. 21 pp. 147–155, 1968; Karabashev, G.S. and Solov'yev, A.N., "Bioluminescence In The Baltic Sea," *Oceanology,* Vol. 12(5), pp. 776–778, 1972]. Some of the bathyphotometers have also measured bioluminescence in the deep scattering layer at varies times of the day and night. [See Kampa, E.M. and Boden, B.P., "Light Generation In A Sonic-Scattering Layer," *Deep Sea Res.,* Vol. 4, pp 73–92, 1956; Clarke, G.L. and Backus, R.H., "Measurements of Light Penetration In Relation To Vertical Migration And Records of Luminescence of Deep-Sea Animals," *Deep-Sea Res.,* Vol. 4, pp. 1–14, 1956; Boden, B.P., "Observations of Bioluminescence On SOND 1965 Cruise of R.R.S. *Discovery,*" *J. Mar. Biol. Assoc. U.K.,* Vol. 49, pp. 669–682, 1969]. To measure bioluminescence from the ocean surface down to 2,000 meters, Clarke and Kelly deployed active bathyphotometers that stimulated luminescence by pumping seawater past a light bathyphotometer window. [Clarke, G.L., and Kelly, M.G., "Measurements of Diurnal Changes In Bioluminescence From The Sea Surface To 2000 Meters Using A Photometric Device," *Limn. and Oceanogr.,* Vol. 10 (suppl.), pp. R54–66, 1965]. They showed that much of the bioluminescence recorded in the top few hundred meters of the ocean was produced by organisms smaller than 0.24 millimeters in diameter, and that larger organisms were responsible for bioluminescence at greater depths.

Surface water bioluminescence has been measured at in harbors and bays by shipboard and towable like bathyphotometers that either count the frequency of bioluminescent flashes or integrate the intensity of light over short periods. [See Backus, R.H., Yentsch, C.S., and Wing, A., "Bioluminescence In The Surface Waters of The Sea," *Nature,* Vol. 192, pp. 518–521, 1961; Seliger, H.H., Fastie, W.G., and McElroy, W.D., "Bioluminescence In Chesapeake Bay," *Science,* Vol. 133, pp. 699–700, 1961; Seliger, H.H., Fastie, W.G., Taylor, W.R., and McElroy, W.D., "Bioluminescence of Marine Dinoflagellates," *J. Gen. Physiol.,* Vol. 45, pp. 1003–1007, 1962; Seliger, H.H. and McElroy, W.D., "Studies At Oyster Bay In Jamaica, West Indies. I. Intensity Patterns of Bioluminescence In A Natural Environment," *J. Mar. Res.,* Vol. 26(3), pp. 244–255, 1968; Carpenter, J.H. and Seliger, H.H., "Studies At Oyster Bay In Jamaica, West Indies. II. Effects of Flow Patterns And Exchange On Bioluminescent Distributions," *J. Mar. Res.,* Vol. 26(3), pp. 256–272, 1968].

More sophisticated on board and submersible photometer systems were developed in the early 1980's at the Naval Ocean Systems Center in San Diego, Calif. [See Losee, J.R. and Lapota, D., "Bioluminescensce Measurements In The Atlantic And Pacific," *Bioluminescence: Current Perspectives,* edited by Nielson, K.H., Burgess Publishing Company, Minneapolis, Minn., pp. 143–152, 1981; Lapota, D., and Losee, J.R., "Observations of Bioluminescence In Marine Plankton From The Sea of Cortez," *J. Exc. Mar. Biol. Ecol.,* Vol. 77, pp. 209–240, 1984; U.S. Pat. No. 4,563,331, by Losee, J.R. and Lapota, D., "System For Measuring Bioluminescence Flash Kinetics," Jan. 7, 1986]. For the on board system, seawater was pumped from a depth of 3 meters from a scientific sea chest through a 25 millimeter internal diameter hose and through a viewing chamber. Two RCA 8575 photomultiplier tubes ("PMT's") with an S-20 response, used in the single photon count mode, were symmetrically mounted on opposite side of the 25 milliliter viewing chamber. These PMT's view bioluminescence through quartz windows that is generated by the fluid turbulence effects on light emitting plankton. This system can be used from an underway or station keeping ship. [See Lapota, supra, 1984]. The submersible system employs the same basic approach of pumping seawater past a photomultiplier tube, but further includes a filter wheel disk which can be remotely rotated so that various filters can be inserted between the quartz window and the photomultiplier tube. This detector can only be utilized from a stationary ship and can measure bioluminescence intensity from the ocean surface down to a depth of 100 meters. [See Lapota, supra, 1984]. Other units similar to these are presently being used in survey operations by the U.S. Naval Oceanographic Office at Bay St. Louis, Miss. A solid state sensor for measuring stimulated bioluminescence was developed to be used in a tow fish called the Undulating Oceanographic Recorder that recorded temperature as well as chlorophyll fluorescence. [Aiken, J., and Kelly, J., "A Solid State Sensor For Mapping And Profiling Stimulated Bioluminescence In The Marine Environment," *Continental Shelf Research,* Vol. 79, pp. 1–14, 1984].

A limitation of all of the above detectors is that they require power supplied either by submarine cables or bulky battery packs that must be recharged before each deployment. A further limitation is that the ships deploying these types of instruments must stop on station in order to maintain the proper cable angle between the ship and the instrument.

Therefore, a need exists for a detector which can detect in situ marine bioluminescence and is deployable from a moving ship.

SUMMARY OF THE INVENTION

The present invention overcomes the limitations of prior art systems by providing an inexpensive bioluminescent probe which can detect in situ marine bioluminescence from the surface to a depth of 150 meters and is deployable from a moving ship by personnel having relatively little training. The invention includes a laminar flow chamber which conducts sea water laden with marine bioluminescent organisms, if present, such as dinoflagellates, into a turbulent flow chamber. The laminar flow chamber is positioned within a forward body which has negative buoyancy. The turbulent flow chamber has at least one aperture which enables sea water to flow out of the turbulent flow chamber back into the ocean. A photon detector circuit mounted within the turbulent flow chamber detects any photons generated by the bioluminescent organisms. A bifilar wire, wound around a spool mounted within the aft body, conducts current between the photon detector circuit and a remote current detecting recording instrument which may be located on board the ship. The current through the photon detector circuit is functionally related to the instantaneously detected photon intensity generated by the microorganisms.

The detector may be launched or deployed from a moving ship into the ocean. Salt water immersion provides a sea water return, enabling the photon detector circuit to become energized by a power supply located on board the ship. Gravity pulls the detector downwardly forcing sea water to flow into and through the laminar flow chamber, into the turbulent flow chamber, and then out of the detector as it descends into the ocean. Turbulent water flow within the turbulent flow chamber causes shear stresses to stimulate bioluminescence of any bioluminescent marine organisms present.

OBJECTS OF THE INVENTION

An object of the present invention is to provide a bioluminescent detector which can be deployed from a moving ship.

Another object of the present invention is to provide a bioluminescent detector which can be deployed by relatively unskilled personnel.

A third object of the present invention is to provide a bioluminescent detector which can provide in situ detection of bioluminescence.

DESCRIPTION OF THE PREFERRED EMBODIMENT

Figure 1:
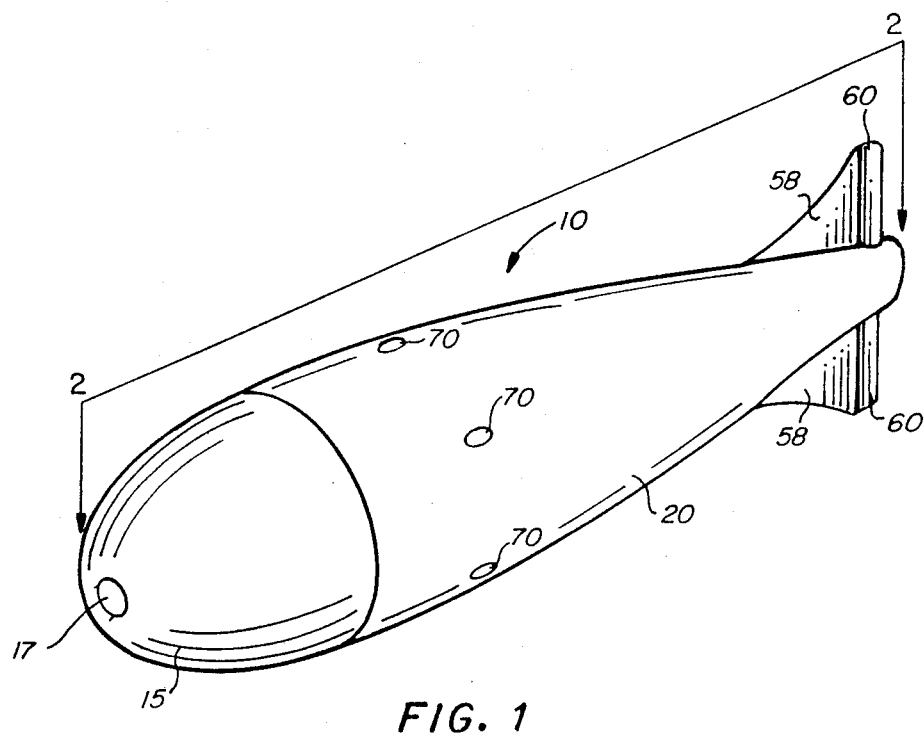
FIG. 1 is a recorder perspective view of the bioluminescent detector looking from the stern towards aft.
Figure 2:
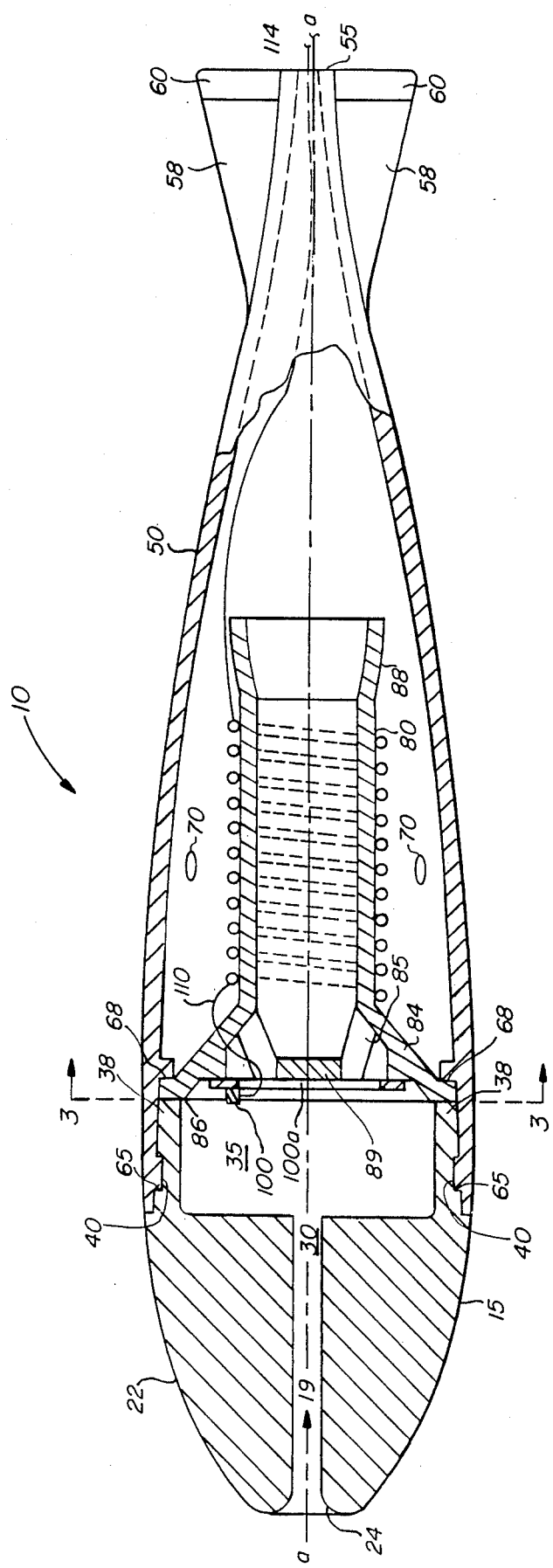
FIG. 2 is a cross-sectional view of the bioluminescent detector.
Figure 4:
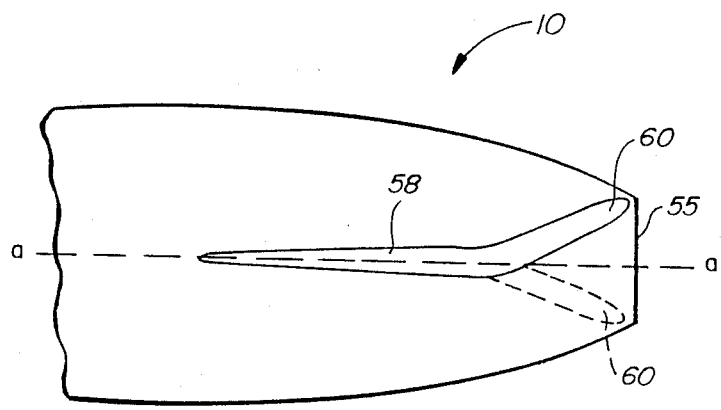
FIG. 4 is a view of the aft end of bioluminescent detector taken along line 4—4 of FIG. 3.

Referring to the drawings where like reference numerals designate like or similar parts throughout the several views, there is illustrated in FIG. 1 bioluminescent detector 10 which includes forward body 15 having laminar flow chamber 17 and aft body 20. Referring to FIG. 2 which illustrates a cross-sectional view of bioluminescent detector 10 taken along plane 2—2 of FIG. 1, forward body 15 has outer surface 22 tapered in the direction of fluid flow, indicated by arrow 19. By way of example, outer surface 22 may define a portion of a conic section such as an ellipse or hyperbola, although other profiles may also be used. Forward body 15 includes gently radiused inlet 24 leading into laminar flow chamber 30. In the preferred embodiment, laminar flow chamber 30 has a circular cross sectional area.

Figure 3:
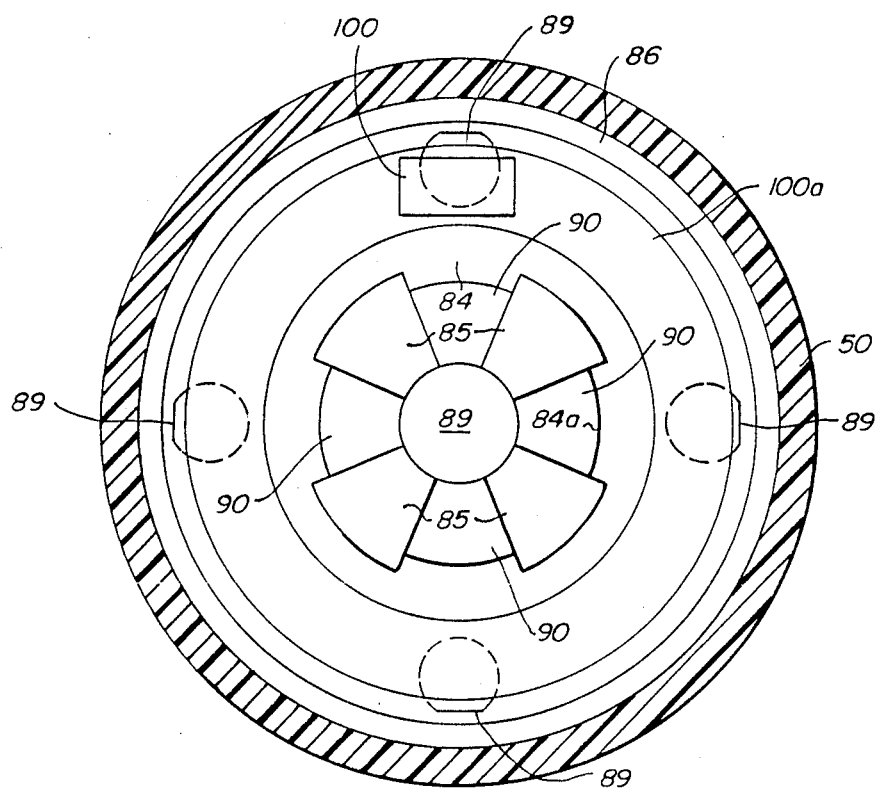
FIG. 3 is a cross-sectional view of the bioluminescent detector taken along section 3—3 of FIG. 2.

Turbulent flow chamber 35, which may have a rectangular cross-sectional area, is formed in aft end 38 of forward body 15 and is in fluid communication with laminar flow chamber 30. Annular groove 40 within forward body 15 is located towards aft end 38. Forward body 15 may be formed of zinc or other material by techniques well known by those skilled in this art and is selected to provide detector 10 with negative buoyancy so that the resultant force of gravity acting on the center of gravity of bioluminescent probe 10 is directed out of inlet 24 of laminar flow chamber 30 along axis a—a. Aft body 50 is gently tapered towards stern 55 so as to provide detector 10 with a minimal drag coefficient. Aft end 55 includes at least two fins 58 projecting perpendicular to axis a—a which have offset surfaces 60 that define an angle bisected by axis a-a, as shown in FIG. 3—3. Aft body 55 is substantially hollow and includes annular tab 65 which is sized to snap-fit conformably within annular groove 40. Aft body 50 also includes at least one and preferably four apertures 70 that provides passages for the egress of air and water. Aft body 50 may be molded from polymeric materials such as ABS, polycarbonate, or polyesters by techniques well known to those skilled in this technology.

Referring to FIG.'s 2 and 3 collectively, bioluminescent detector 10 also includes spool 80 which may be molded of the same materials as is aft body 50. Spool 80 includes funnel shaped, annular conical support 84 having inner circular periphery 84a from which four radial spokes 85 radiate inwardly and forward to apex 89. The spaces between spokes 85 define apertures 90 through which water may flow. Four mounting pads 89a, which may be spaced 90 degrees apart, extend forward from support 84. Photon detector circuit 100 is mounted to annular shaped circuit board 100a by means well known to those skilled in this art, as for example, by use of a suitable adhesive. Circuit board 100a is mounted to pads 89, as for example, also by the use of a suitable adhesive, or by use of circuit mounting tabs, not shown. Bifilar wire 110 is operably connected to photon detector circuit 100, threaded through one of the apertures 90, and is wrapped in a coil around spool 80. Wire 110 pays out through aperture 114 in stern end 55 of aft body 50 and is connected to electrical apparatus as described more fully herein.

Bioluminescent detector 10 is assembled by placing spool 80 into the interior of aft body 50 so that aft end 88 of spool 80 faces aft end 55 of aft body 50. Flange 86 of spool 80 is positioned on annular land 68. Forward and aft bodies 15 and 50 are joined by snap-fitting annular tab 65 into annular groove 40.

Figure 5:
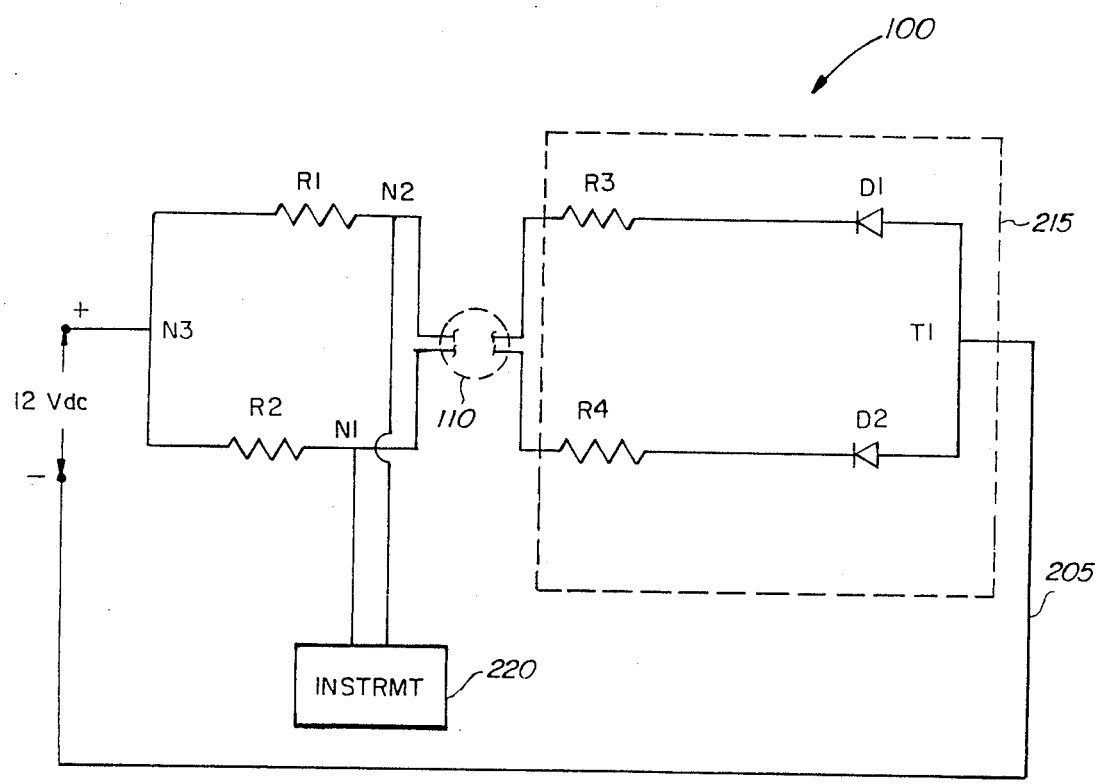
FIG. 5 is a schematic diagram of the photon detector circuit.

Referring to FIG. 5, there is illustrated photon detector circuit 100 which includes the parallel combination of resistors R1 and R2 which provide a voltage divider bridge at nodes N1 and N2. Resistor R is connected in series with diode D1. Resistor R4 is connected in series with diode D2. Diodes D1 and D2 are reversed biased so that the current through each of them is dependent upon: the applied voltage; the resistance of the series resistor strings that include resistors R1 and R3, and R2 and R4; the resistance of the seawater link; the light impinging on diodes D1 and D2; and the temperature of each diode. The resistances of the resistor strings are identical, the temperature of each diode is identical, and the applied voltage to each string is identical.

One of diodes D1 or D2 is blanked with an optically opaque substance such as epoxy, paint, or other material. Diode D1 and resistors R3 and R4 comprise a first diode leg. Diode D2 and resistors R2 and R4 comprise a second diode leg. The blanked diode provides photon detector circuit 100 with temperature compensation. The diode leg with the blanked diode compensates for resistance variabilities associated with wire length, salinity and other aspects of the seawater link and temperature. The only remaining variable between the two diode legs is the light that may impinge on the remaining diode that is not blanked. This latter diode is positioned so that it can detect any photons generated within turbulent flow chamber 35. The resistance of whichever photodiode, D1 or D2 that is not blanked, decreases as detected light intensity increases. The differential current between the two diode legs appears as a voltage difference between nodes N1 and N2. Photon detector circuit 100 is divided into a ship based portion shown to be outside the area defined by dotted rectangle 215 and portion located on detector 10 shown to be within the area defined by rectangle 215. Electrical power is provided from a ship based power supply, which may be 12 vdc, to node N3 between resistors R1 and R2. Terminal T1 is an open contact connected between diodes D1 and D2 and is coupled to sea water return 205 when photon detector circuit 100 is immersed in sea water. One of diodes D1 or D2 is blanked, as for example, by being wrapped in electrical tape so as to isolate it from any light. This isolation is necessary in order for photon detector circuit 100 to function independently of ambient temperature which might otherwise affect the output of circuit 100. Bifilar wire 110 is connected between nodes N1 and N2 and a ship based instrument 220 which can sense the change in current between nodes N1 and N2. Instrument 220 provides an output which is functionally related to the instantaneously detected intensity of any photons generated within turbulent flow chamber 35. By way of example, bifilar wire 110 may be sized as AWG 39 gage. Photon detector circuit 100 may be implemented as an integrated circuit, as a hybrid integrated circuit, or as discrete components.

In the preferred embodiment, photodiodes D1 and D2 may be United Detector Technology Model No. PIN5D097-1 which are modified by having their plastic lenses removed. A cavity in each photodiode results from removing the lenses that then is filled with a clear optical epoxy. Suitable epoxies include No. 301-2 by Epoxy Technology, Inc. and No. UV10 by Master Bond, Inc. The epoxy makes the photodiode pressure tolerant. The critical parameters of photo diodes D1 and D2 are that they provide peak output in the range of approximately 480–490 nanometers, which is the wavelength of light given off by bioluminescent organisms such as dinoflagellates and microplankton. The response time of photo diodes D1 and D2 is approximately 15 nanoseconds which is many orders of magnitude less than the response time of the bioluminescent organisms, typically about 20–60 milliseconds. Thus, photodiodes D1 and D2 are quick enough to detect any photons given off by the organisms. Although specific models of photodiodes have been identified, the scope of the invention comprehends the use of other photodiodes, besides those specifically mentioned, having performance characteristics similar to those referenced above, that may be similarly modified to enable them to be pressure tolerant so that they function at varying water depths.

In the operation of the invention, bioluminescent detector 10 is dropped over the side of a ship, which may be underway, into seawater, forward body down. As the force of gravity pulls bioluminescent detector downward, the drag coefficient of bioluminescent probe causes the probe to descend at constant velocity. When bioluminescent detector 10 enters the ocean, open metal contact T1 becomes electrolytically connected to the anode of the electrical power supply on board the ship, thus energizing photon detector circuit 100. Ocean water flowing over surfaces 60 is deflected causing bioluminescent detector 10 to spin about axis a—a which enables bifilar wire 110 to pay out smoothly from spool 80. As bioluminescent detector 10 descends, seawater is forced through inlet 24 into laminar flow chamber 30 and enters turbulent flow chamber 35 where shear stresses generated by the turbulence cause any bioluminescent organisms present to generate photons. Any air entrained within bioluminescent detector 10 is displaced by the ocean through apertures 90, 114, and 70. The seawater exits turbulent flow chamber 35 through apertures 90 in conical support 84 and out of aft body 50 through aperture 114. Any photons emitted by the bioluminescent organisms are detected by either photodiode D1 or D2, whichever one is not blanked out, causing the resistance of that photodiode to decrease and hence change the current through bifilar wire 112. This change in current is detected by instruments located on board ship and is functionally related to the instantaneous intensity of detected photons.

Obviously many modifications and variations of the present invention are possible in light of the above teachings. It is therefore to be understood within the scope of the appended claims the invention may be practiced otherwise than as specifically described. For example, the present invention has been described as being deployable from a moving ship, however, bioluminescent detector 10 may also be deployed from an aircraft or shore based facility.

We claim:

1. A bioluminescent detector, comprising:
   a laminar flow chamber having a gently radiused inlet port and an outlet port;
   a turbulent flow chamber having an inlet port and at least one outlet port, said inlet port of said turbulent flow chamber being in fluid communication with said outlet port of said laminar flow chamber; and
   a photon detecting network means mounted within said turbulent flow chamber for detecting photons within said turbulent flow chamber, said photon detecting network means providing an output functionally related to the intensity of the detected photons.

2. The detector of claim 1 which further includes:
   conducting means operably coupled to said photon detecting network means for conducting said output of said photon detecting means to a remote instrument.

3. The detector of claim 2 wherein said photodetecting network means includes:
   at least one photodiode.

4. The detector of claim 3 wherein:
   said at least one photodiode has a resistance which varies in response to said at least one photodiode being illuminated by light having a wavelength ranging from about 420 to 620 nanometers.

5. The detector of claim 4 wherein:
   said conducting means is electrically conductive.

6. The detector of claim 5 wherein:

said laminar flow chamber is located within a forward body having a tapered profile.

7. The detector of claim 6 which further includes:
an aft body mounted to said forward body, said aft body being substantially hollow, having an exterior surface, and having an outlet aperture at a stern end;
a spool mounted within said aft body, whereby said conducting means is coiled around said spool and is threaded through said outlet aperture of said aft body; and
at least two fins extending from said surface of said aft body, said fins each having an offset area.

8. The detector of claim 7 wherein:
said forward body has negative buoyancy.

9. A bioluminescent detector, comprising:
a laminar flow chamber having an inlet port and an outlet port;
a turbulent flow chamber having an inlet port and at least one outlet port said inlet port of said turbulent flow chamber being in fluid communication with said outlet port of said laminar flow chamber;
photon detecting network means mounted within said turbulent flow chamber for detecting photons within said turbulent flow chamber, said photon detecting network means providing an output functionally related to the intensity of the detected photons, said photodetecting detecting network means including first and second photodiodes, said first photodiode being operably connected to said second photodiode, said first photodiode being within an opaque covering, said photon detecting network means including means for reverse biasing said first photodiode with respect to said second photodiode; and conducting means operably coupled to said photon detecting network means for conducting said output of said photon detecting means to a remote instrument.

10. The detector of claim 9 wherein said photodetecting network means further includes:
a first resistor operably connected to said first photodiode; and
a second resistor operably connected to said second photodiode.

11. The detector of claim 10 which further includes:
a first electrical wire operably connected to said first resistor; and
a second electrical wire operably connected to said second resistor.

12. The detector of claim 11 wherein:
said laminar flow chamber is located within a forward body having a tapered profile.

13. The detector of claim 12 which further includes:
an aft body mounted to said forward body, said aft body being substantially hollow, having an exterior surface, and having an outlet aperture at a stern end;
a spool mounted within said aft body, whereby a bifilar wire is coiled around said spool and is threaded through said outlet aperture of said aft body; and
at least two fins extending from said surface of said aft body, said fins each having an offset area.

14. The detector of claim 13 wherein:
said forward body has negative buoyancy.

15. A bioluminescent detector, comprising:
a laminar flow chamber having a gently radiused inlet port, an outlet port, a cross-sectional area, and a longitudinal axis;
a turbulent flow chamber having an inlet port, an at least one outlet port, a longitudinal axis collinearly aligned with said longitudinal axis of said laminar flow chamber, and a cross-sectional area greater than said cross-sectional area of said laminar flow chamber, said inlet port of said turbulent flow chamber being juxtaposed to and in fluid communication with said outlet port of said laminar flow chamber; and
photon detecting network means mounted within said turbulent flow chamber for detecting photons within said turbulent flow chamber, said photon detecting network means providing an output functionally related to the intensity of the detected photons.

16. The detector of claim 15 which further includes:
conducting means operably coupled to said photon detecting network means for conducting said output of said photon detecting means to a remote instrument.

17. The detector of claim 16 wherein said photodetecting network means includes:
at least one photodiode.

18. The detector of claim 17 wherein:
said at least one photodiode has a resistance which varies in response to said at least one photodiode being illuminated by light having a wavelength ranging from about 420 to 620 nanometers.

19. The detector of claim 18 wherein:
said conducting means is electrically conductive.

20. The detector of claim 19 wherein:
said laminar flow chamber is located within a forward body having a tapered profile.

21. The detector of claim 20 which further includes:
an aft body mounted to said forward body, said aft body being substantially hollow, having an exterior surface, and having an outlet aperture at a stern end;
a spool mounted within said aft body, whereby said conducting means is coiled around said spool and is threaded through said outlet aperture of said aft body; and
at least two fins extending from said surface of said aft body; said fins each having an offset area.

22. The detector of claim 21 wherein:
said forward body has negative buoyancy.

23. A bioluminescent detector, comprising:
a forward body;
a laminar flow chamber having an inlet port and an outlet port, said laminar flow chamber being located within said forward body;
a turbulent flow chamber having an inlet port and at least one outlet port, said inlet port of said turbulent flow chamber being in fluid communication with said outlet port of said laminar flow chamber;
photon detecting network means mounted within said turbulent flow chamber for detecting photons within said turbulent flow chamber, said photon detecting network means providing an output functionally related to the intensity of the detected photons, said photon detecting means including at least one photodiode having a resistance which varies in response to said at least one photodiode being illuminated by light having a wavelength ranging from about 420 to 620 nanometers;

electrically conducting means operably coupled to said photon detecting network means for conducting said output of said photon detecting means to a remote instrument;

an aft body mounted to said forward body, said aft body being substantially hollow, having an exterior surface, and having an outlet aperture at a stern end;

a spool mounted within said aft body, whereby said conducting means is coiled around said spool and is threaded through said outlet aperture of said aft body; and at least two fins extending from said surface of said aft body, said fins each having an offset area.

24. The detector of claim 23 wherein:
said forward body has negative buoyancy.

25. A bioluminescent detector, comprising:
a forward body having a tapered profile;
a laminar flow chamber having an inlet port and an outlet port, said laminar flow chamber being located within said forward body; a turbulent flow chamber having an inlet port and at least one outlet port, said inlet port of said turbulent flow chamber being in fluid communication with said outlet port of said laminar flow chamber;

photon detecting network means mounted within said turbulent flow chamber for detecting photons within said turbulent flow chamber, said photon detecting network means providing an output functionally related to the intensity of said detected photons, said photodetecting detecting network means including first and second photodiodes, said first photodiode being operably connected to said second photodiode, said first photodiode having an opaque covering, said photon detecting network means including means for reverse biasing said first photodiode with respect to said second photodiode, said photon detecting network means further including a first resistor operably connected to said first photodiode and a second resistor operably connected to said second photodiode;

conducting means operably coupled to said photon detecting network means for conducting said output of said photon detecting means to a remote instrument;

a first electrical wire operably connected to said first resistor;

a second electrical wire operably connected to said second resistor;

an aft body mounted to said forward body, said aft body being substantially hollow, having an exterior surface, and having an outlet aperture at a stern end;

a spool mounted within said aft body, whereby a bifilar wire is coiled around said spool and is threaded through said outlet aperture of said aft body; and at least two fins extending from said surface of said aft body, said fins each having an offset area.

26. The detector of claim 25 wherein:
said forward body has negative buoyancy.

* * * * *